US011541248B2

(12) United States Patent
Chabrol et al.

(10) Patent No.: US 11,541,248 B2
(45) Date of Patent: Jan. 3, 2023

(54) IMPLANTABLE LOCALISED ILLUMINATING DEVICE WITH IMPROVED ARCHITECTURE

(71) Applicant: COMMISSARIAT A L'ENERGIE ATOMIQUE ET AUX ENERGIES ALTERNATIVES, Paris (FR)

(72) Inventors: Claude Chabrol, Poisat (FR); Sarah Renault, Corenc (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/771,464

(22) PCT Filed: Dec. 3, 2018

(86) PCT No.: PCT/FR2018/053084
§ 371 (c)(1),
(2) Date: Jun. 10, 2020

(87) PCT Pub. No.: WO2019/115909
PCT Pub. Date: Jun. 20, 2019

(65) Prior Publication Data
US 2021/0069522 A1 Mar. 11, 2021

(30) Foreign Application Priority Data

Dec. 11, 2017 (FR) .................................... 1761885
Dec. 11, 2017 (FR) .................................... 1761886
Dec. 11, 2017 (FR) .................................... 1761888

(51) Int. Cl.
A61N 5/06 (2006.01)

(52) U.S. Cl.
CPC ......... A61N 5/0601 (2013.01); A61N 5/0613 (2013.01); A61N 2005/0664 (2013.01)

(58) Field of Classification Search
CPC .................................................... A61N 5/0601
See application file for complete search history.

(56) References Cited

U.S. PATENT DOCUMENTS 4,652,143 A 3/1987 Wickersheim et al.
5,304,171 A * 4/1994 Gregory ............... A61B 18/245
385/125

(Continued)

FOREIGN PATENT DOCUMENTS

WO WO 86/03293 A1 6/1986
WO WO 2007/120678 * 10/2007

(Continued)

OTHER PUBLICATIONS

International Search Report dated Feb. 19, 2019 in PCT/FR2018/053084 filed on Dec. 3, 2018, 3 pages.

Primary Examiner — Nathan J Jenness
Assistant Examiner — Skylar Lindsey Christianson
(74) Attorney, Agent, or Firm — Oblon, McClelland, Maier & Neustadt, L.L.P.

(57) ABSTRACT

The invention relates to an implantable illuminating device intended to be implanted in a living being with a view to locally illuminating a region of said living being, said device including a probe, said architecture being characterized in that it is produced from: an optical fiber that comprises a core, a cladding and a protective coating, a jacket, said architecture including: a plurality of successive segments along its longitudinal axis, each segment having a section containing a plurality of concentrically superposed layers, in which each segment includes a section containing a plurality of superposed layers that is different from the section of each adjacent segment.

15 Claims, 5 Drawing Sheets

(56) References Cited

U.S. PATENT DOCUMENTS

| | | | |
|---|---|---|---|
| 7,003,184 B2 * | 2/2006 | Ronnekleiv | A61B 5/01 385/12 |
| 2007/0282404 A1 | 12/2007 | Cottrell et al. | |
| 2009/0221921 A1 | 9/2009 | Cottrell et al. | |
| 2012/0136385 A1 * | 5/2012 | Cully | A61M 25/0662 606/194 |
| 2014/0074182 A1 * | 3/2014 | Wolf, II | A61N 1/3616 607/46 |
| 2015/0273236 A1 * | 10/2015 | Rogers | A61N 5/0624 607/80 |
| 2017/0361122 A1 | 12/2017 | Chabrol et al. | |
| 2019/0008376 A1 | 1/2019 | Wortelboer et al. | |

FOREIGN PATENT DOCUMENTS

| | | |
|---|---|---|
| WO | WO 2007/120678 A2 | 10/2007 |
| WO | WO 2007/120678 A3 | 10/2007 |
| WO | WO 2016/102351 A1 | 6/2016 |
| WO | WO 2017/025423 A1 | 2/2017 |

\* cited by examiner

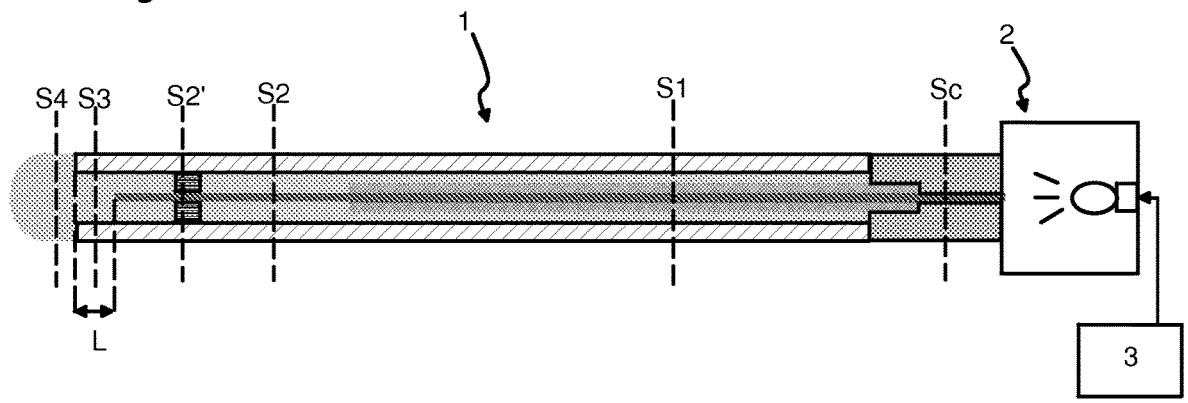
Fig. 1A
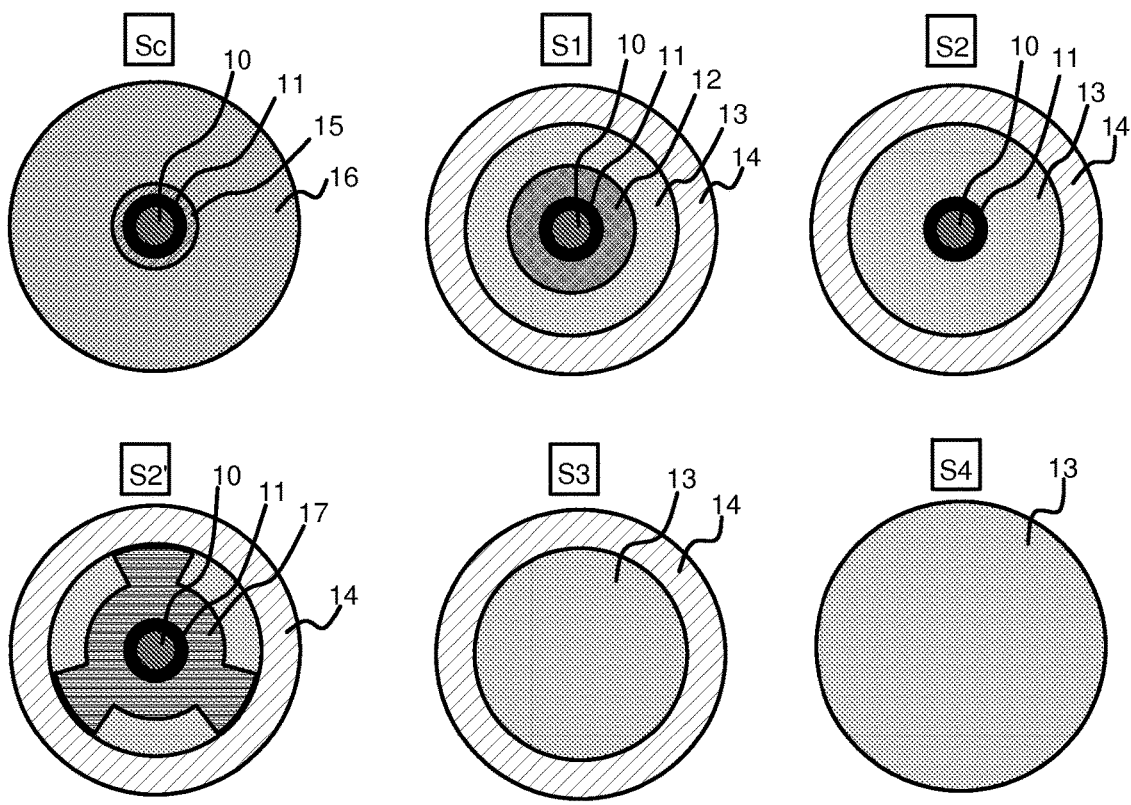

*Fig. 5*
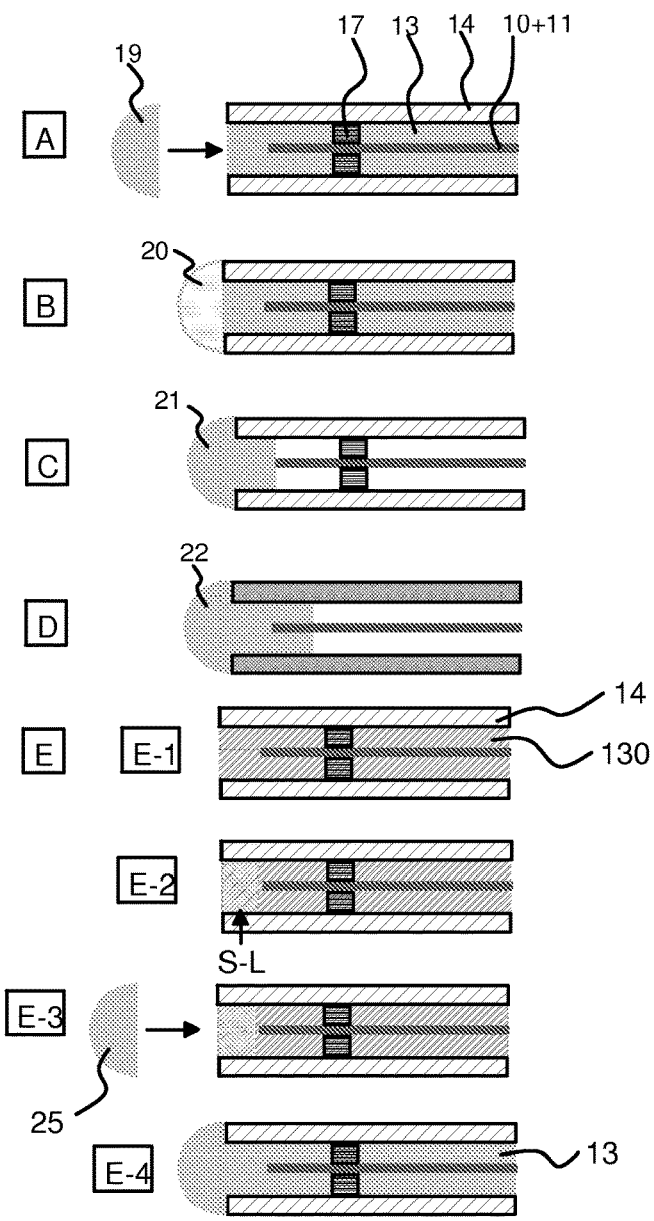
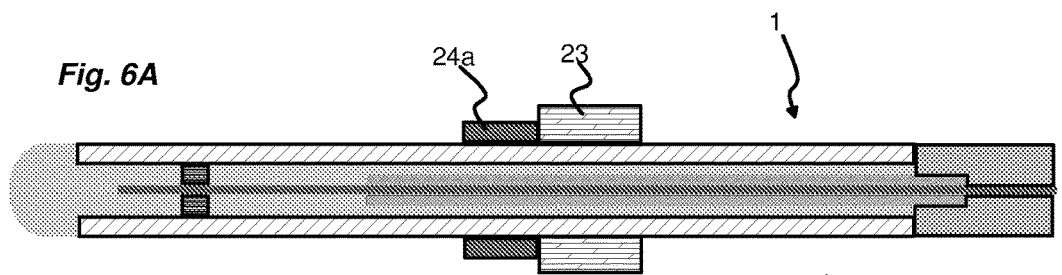
*Fig. 6A*
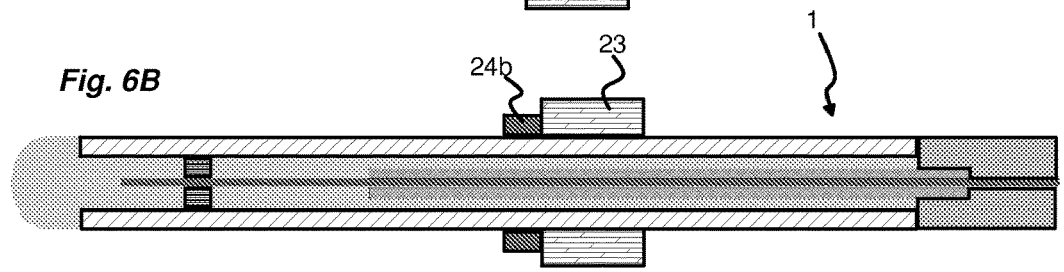
*Fig. 6B*

IMPLANTABLE LOCALISED ILLUMINATING DEVICE WITH IMPROVED ARCHITECTURE

CROSS-REFERENCE TO RELATED APPLICATION

The present application is a national stage application of PCT Application No: PCT/FR2018/053084, filed Dec. 3, 2018, which claims priority to French Patent Application Nos. 17 61885, 17 61886, and 17 61888, all filed on Dec. 11, 2017. The benefit of priority is claimed to each of the foregoing, and the entire contents of each of the foregoing are incorporated herein by reference.

TECHNICAL FIELD OF THE INVENTION

The present invention relates to an illuminating device intended to be at least partially implanted into a living being with a view to locally illuminating at least one region of the living being.

PRIOR ART

To treat certain pathologies of a living being, it has been imagined to stimulate an internal region of a living being optically. To do this, devices have been proposed that comprise a light source and that are at least partially or entirely implanted into the living being with a view to illuminating the desired region.

The advantage of such devices when it is a question of illuminating/irradiating certain regions of the human brain optically have notably been observed.

However, on account of risks related to the implantation of such a device in the brain, it will be understood that such a device must be perfectly designed.

Such a device is known from patent application US2012/259393A1. The solution presented in this document is not faultless.

Another solution is known from patent application WO2016/102351A1. The solution presented in this documents proves to be inflexible and difficult to implement without risk of lesions to the tissues of the implanted patient.

Other solutions are also described in documents US2014/074182A1 and U.S. Pat. No. 7,003,184B2.

The aim of the invention is to provide an illuminating device intended to be at least partially implanted in a living being, notably with a view to illuminating one or more regions of its brain, said device having an architecture suitable for playing such a role. It will notably have to meet one or more of the following objectives:
- employ bio-compatible materials;
- minimize medical risks during its implantation and explantation;
- ensure the physical and esthetic comfort of the patient;
- be easy to manufacture and of easily reproducible manufacture;
- allow an effective treatment.

SUMMARY OF THE INVENTION

This aim is achieved via an implantable illuminating device intended to be implanted in a living being with a view to locally illuminating a region of said living being, said device comprising a probe having an architecture that is elongate along an axis between a near end and a far end, said probe taking the form of a rod of circular section of constant diameter over all its length, said architecture being produced from:
- a stimulating optical fiber that comprises a core, a cladding and a protective coating,
- a jacket,
- said architecture comprising:
- a plurality of successive segments along its longitudinal axis, each segment having a section containing a plurality of concentrically superposed layers, in which each segment comprises a section containing a plurality of superposed layers that is different from the section of each adjacent segment,
- at least a first segment along which said stimulating optical fiber is jacketed by the jacket,
- at least a second segment extending said first segment, in which said stimulating optical fiber is stripped to remove its protective coating so as to leave behind only its core and its optical cladding jacketed by the jacket,
- at least a terminal segment the section of which comprises only said jacket, said terminal segment comprising the far end of the probe and in that this far end is configured so as to be atraumatic.

According to a first particular embodiment, the section of the first segment comprises a first layer comprising the optical-fiber core, a second layer comprising the optical-fiber cladding, a third layer comprising the protective optical-fiber coating, a fourth layer comprising the jacket and an external fifth layer composed of a tube.

According to one particularity of this first embodiment, the section of the second segment extending said first segment and the section of which comprises a first layer comprising the core of said optical fiber, a second layer formed from the cladding of the optical fiber, and a third layer comprising said jacket, the device also comprises a fourth layer comprising said tube.

According to another particularity of this first embodiment, the device comprises a third segment extending said second segment and the section of which comprises a first layer comprising said jacket and a second layer comprising said tube.

According to another particularity of this first embodiment, the tube is made from a radiopaque material.

According to a second particular embodiment, the section of the first segment comprises a first layer comprising the optical-fiber core, a second layer comprising the optical-fiber cladding, a third layer comprising the protective optical-fiber coating and a fourth layer comprising the jacket which is over-molded on the optical fiber.

According to one particularity of this second embodiment, the second segment extends said first segment and has a section that comprises solely a first layer comprising the core of said optical fiber, a second layer formed from the cladding of the optical fiber, and a third layer comprising said jacket.

According to one particularity of the device, it comprises a connecting segment, located upstream of the first segment, the section of which comprises a first layer formed from the core of the fiber, a second layer formed from the optical-fiber cladding, a third layer formed from an adhesive and a fourth layer formed from a ferule.

According to another particularity, the device comprises a light source to which is optically connected said probe via its near end.

According to another particularity, the device comprises a stopping member associated with at least one spacer in order to adjust the penetration of the probe and the position of its far end.

According to another particularity, the device comprises at least one member for centering said stripped stimulating optical fiber, said member being positioned around said optical fiber and arranged to form a shim for said stripped optical fiber According to another particularity, said centering member comprises a cylindrical sleeve having a central channel in which is inserted said stripped optical fiber.

According to another particularity, said sleeve comprises one or more external lateral grooves.

According to one variant embodiment, said centering member comprises a part of helical shape that is wound around the core of the optical fiber and its cladding.

According to one particularity, said centering member is made of a radiopaque material.

According to one particularity, the device comprises an optical feedback system comprising at least a first feedback optical fiber comprising an input optical end configured to capture an optical signal and an output optical end configured to transmit the captured optical signal, said first feedback optical fiber being wound helically around the stimulating optical fiber over at least one portion of the length of said stimulating optical fiber.

According to another particularity, the optical feedback system comprises a second feedback optical fiber wound helically around said stimulating optical fiber and comprising an input optical end and an output optical end.

According to another particularity, the input optical end of the first feedback optical fiber and the input optical end of the second feedback optical fiber are located at different lengths from the optical output of the stimulating optical fiber.

According to another particularity, each feedback optical fiber comprises a core of circular section and an optical cladding having a substantially square section, having two curved opposite sides, one of these two sides having a first radius of curvature and the other of these two opposite sides having a second radius of curvature different from the first radius of curvature.

The invention also relates to a process for fabricating an implantable illuminating device such as defined above in its first particular embodiment, said process comprising the following steps:
- filling the tube with un-crosslinked jacket material,
- at least partially drying the un-crosslinked jacket material in order to set it inside the tube,
- depositing a calibrated amount of un-crosslinked jacket material in order to form said terminal segment,
- crosslinking the jacket material over the entire length of the probe.

BRIEF DESCRIPTION OF THE FIGURES

Other features and advantages will become apparent from the following detailed description, which is given with reference to the appended drawings, which are listed below:

FIG. 1A shows, seen via an axial longitudinal cross section and a plurality of transverse cross sections, the architecture of the implantable illuminating device of the invention, according to a first embodiment;

FIG. 5 illustrates various solutions for producing the optical output;

FIGS. 6A and 6B illustrate a principle of adjustment of the position of the probe.

DETAILED DESCRIPTION OF AT LEAST ONE EMBODIMENT

Figure 1B:
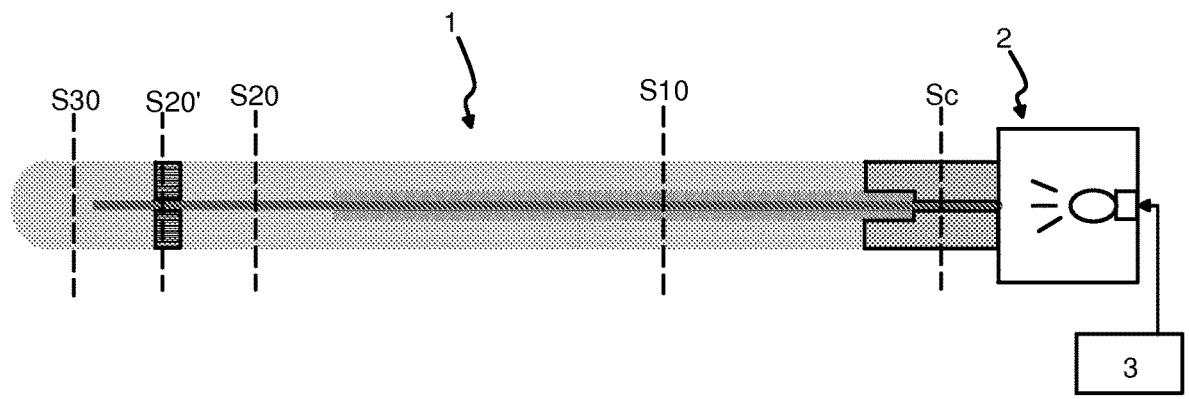
FIG. 1B shows, seen via an axial longitudinal cross section and a plurality of transverse cross sections, the architecture of the implantable illuminating device of the invention, according to a second embodiment
Figure 1B:
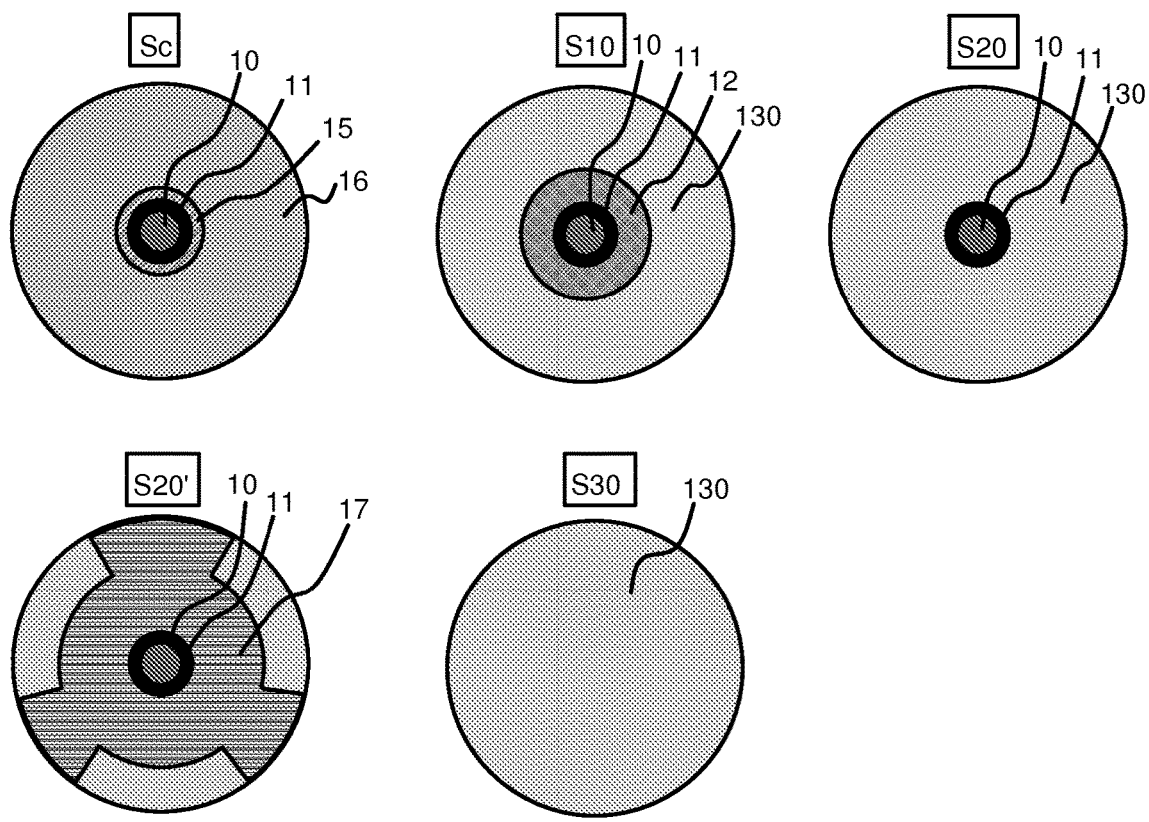

The invention relates to an implantable illuminating device.

It will have the objective of producing an illumination of tissues with the aim of neuro-protection, of stimulation, or with an opto-genetic aim.

The device will notably be perfectly suitable for ensuring a ventricular illumination of the brain locally. It will possibly serve in the treatment of neurodegenerative diseases such as Parkinson's disease. Of course, it will possibly be applied to other pathologies and will possibly be employed for an implantation into any region of the body of a living being.

The device is advantageously described for the optical stimulation of a region of the brain.

The particularity of the device of the invention is notably to allow an optical stimulation from a supple solution, thin enough (1 to 2.5 mm, ideally comprised between 1.25 and 1.3 to be suitable for DBS (deep brain stimulation) apparatuses) to be inserted into the third ventricle or into contact with any other region of the brain accessible surgically without stereotactic tools, once a ventricular catheter or guide (Renishaw neuro-guide or ventricular catheter equipped with a Rickham-Ommaya reservoir, or any other suitable guiding solution) has been positioned beforehand between the skull and the third ventricle.

The device comprises a probe 1. The probe 1 has an architecture that is elongate along a longitudinal axis when said architecture is not dog-legged. In other words, the probe takes the form of a rod having a certain degree of flexibility and of elastic deformation. The rod thus comprises two ends, a near end forming an optical input intended to receive light radiation from a light source 2 and a far end comprising an optical output via which the light radiation is transmitted in the direction of the region to be illuminated/treated.

The probe will be able to flexurally deform elastically to make an angle comprised between 30° and 110° with respect to its right initial shape in the rest state, and preferably of 90° so as then to form a dog-leg at the point of passage between the exterior of the skull and the brain.

The light source 2 advantageously forms part of the device.

The source will be able to emit in a wavelength range comprised between 650 nm and 1070 nm in the context of neuroprotection or 450 nm to 650 nm for optogenetics. The source 2 will advantageously be powered by a battery and controlled by a control unit 3 so as to generate a DC electrical current or pulses at a given frequency. The source will possibly be integrated into a neuro-stimulator or be located remotely.

The light source 2 may be a laser diode, a light-emitting diode or any other solution suitable for optical coupling to the probe.

The control unit 3 of said light source 2 advantageously forms part of the device.

The light source 2 and the control unit 3 may be placed together in the same housing.

The device may comprise an optical base connected to the light source.

The optical base may be arranged in said housing.

The probe 1 comprises a complementary connector forming its optical input, arranged to connect to (disconnect from, respectively) said optical base.

The rod forming the probe 1 advantageously has a circular section of outside diameter that will possibly be comprised between 1 and 2.5 mm depending on the embodiment.

The device has a perfectly seal-tight architecture. The diameter of the probe is advantageously constant over the entire length of the probe (except level with its stopping system—see below).

The end of the probe forming the optical output advantageously has a shape that is said to be atraumatic. It is a question of giving it a shape without protruding edges. It could be for example a hemispherical shape, an oblong shape, or an equivalent shape.

Along its axis, the architecture of the probe 1 has a section the composition of which, which contains a plurality of concentric layers, varies.

The probe thus comprises a plurality of successive segments (Sc to S4 or Sc to S30) between its optical input and its optical output. Each segment has a specific structure containing a plurality of concentric layers.

The probe comprises an optical fiber.

Figure 2:
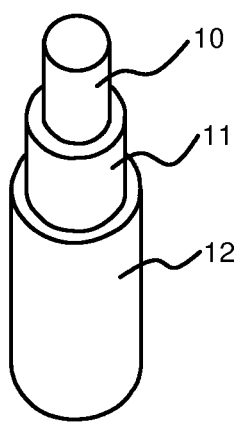
FIG. 2 shows the multilayer structure of an HCS optical fiber.

With reference to FIG. 2, the optical fiber may comprise a core 10 made of silica, sapphire or plastic (acrylate or any other suitable material) and an optical cladding 11 produced around the core.

The cladding may be made of plastic, for example from a fluoro-acrylate material, from a material such as silica or any other material of suitable index.

The optical fiber may comprise a protective mechanical coating 12 around its cladding.

The protective coating 12 may be made from a material such as ethylene tetrafluoroethylene (ETFE).

It will thus be a question of providing, for example, a hard clad silica (HCS) optical fiber. Of course, any other architecture could be envisioned.

However, there is a risk with this type of fiber of debonding between its ETFE coating and its fluoro-acrylate cladding.

To remedy this risk and to improve the suppleness of the probe, it is proposed to strip over a sufficient length (for example 5 to 70 mm) the fiber on the far side. The optical fiber is thus stripped to remove its protective coating 12 and to preserve only its core and its optical cladding.

The stripping length is chosen depending on the length implanted into the brain, for example 70 mm to reach the floor of the $3^{rd}$ ventricle.

Advantageously, it is also proposed to strip the portion of the optical fiber adhesively bonded to the ferule near the optical input in order to guarantee a good centeredness of the fiber in this connector.

In the rest of the description, the silicone employed to produce the device may be replaced by a supple material such as polyurethane having the same qualities, notably the same optical qualities and the same qualities with respect to stability over time. However, for the sake of simplicity, we will refer to silicone.

Based on the fiber such as described above, two different embodiments are envisionable.

In a first embodiment, the probe comprises a tube 14, for example made of silicone, defining a central channel. The outside diameter of the section of the tube 14 defines the maximum diameter of the section of the probe (excluding level with its stopping system—see below). The silicone forming the tube is chosen to have suitable mechanical characteristics. It may be optical-grade or not (i.e. transparent or opaque). By way of example, the tube will be made of MED 4765 silicone.

The optical fiber is inserted into the central channel of the tube 14. Over the entire length of the probe, silicone 13 is advantageously added to the tube 14, via injection or any other manufacturing process, so as to coat the various elements present in the tube and thus ensure that the probe is perfectly seal-tight with respect to the treated region. This injected silicone is advantageously optical-grade (i.e. it is optically transparent and has a refractive index that matches the core of the optical fiber and the physiological liquid—refractive index comprised between 1.33 and 1.46, preferably 1.41—MED 6233 silicone).

The fiber may be treated beforehand (primer, plasma treatment, etc.) to guarantee a good adherence of the silicone 13, 130 during the manufacture.

In a second embodiment, silicone is over-molded directly around the fiber, so as to coat it. The silicone over-molded around the fiber thus ensures the probe is perfectly seal-tight with respect to the treated region.

First Embodiment—FIG. 1A

Non-limitingly, with reference to FIG. 1A, in the first embodiment mentioned above, the probe thus comprises various segments, each segment having a specific cross section. This architecture thus allows various levels of flexibility, of mechanical protection and of seal-tightness to be given to the probe along its axis.

Starting from the internal layer closest to the axis and moving toward the external layer, which is the layer furthest from the axis of the probe, the various segments are described below.

The probe comprises a connecting segment (section Sc) advantageously forming the optical input of the device.

The connecting segment comprises:
- a first layer formed from the core 10 of the optical fiber;
- a second layer formed from the cladding 11 of the optical fiber;
- a third layer formed from an epoxy adhesive 15;
- a fourth layer formed from a ferrule 16 allowing the optical connection to the light source; the epoxy adhesive allows the ferrule to be adhesively bonded to the second layer (cladding of the optical fiber). In this connecting segment, it is proposed to strip the optical fiber over at least one portion of its length in order to remove its protective coating and allow the ferrule to be adhesively bonded.

The probe comprises a first segment (section S1) extending the connecting segment.

This first segment solely comprises:
- a first layer formed from the core 10 of the fiber;
- a second layer formed from the cladding 11 of the optical fiber;

a third layer formed from the protective coating 12 of the optical fiber;

a fourth layer composed of the silicone jacket 13;

a fifth layer formed from the tube 14.

This first segment is intended to remain in the extra-cortical region of the living being and will be bent during its implantation to form a dog-leg therein. The first layer, the second layer and the third layer form the optical fiber such as described above. To improve the mechanical protection, the protective coating of the fiber is kept in this first segment.

The probe comprises a second segment (section S2) extending the first segment in the direction extending from the optical input to the optical output of the probe.

This second segment solely comprises:

a first layer formed from the core 10 of the fiber;

a second layer formed from the cladding 11 of the optical fiber;

a third layer formed from the silicone jacket 13;

a fourth layer formed from the tube 14.

The second layer is intended to penetrate into the intracerebral region. It is in this second segment that the optical fiber is stripped to remove its protective coating 12, thus allowing this segment to be made more supple and more seal-tight.

The probe comprises a third segment (section S3) extending the second segment in the direction extending from the optical input to the optical output of the probe.

This third segment solely comprises:

a first layer formed from the silicone jacket 13;

a second layer formed from the tube 14.

It will thus be noted that the end of the optical fiber defines the end of the second segment and that the tube 14 extends into the third segment S3. The length L (typically 1.5 mm to 2.5 mm) between the end of the tube 13 and the end of the core 10 of the fiber at the far end, notably allows the power density output from the probe to be adjusted.

The probe comprises a fourth segment (section S4) extending the third segment in the direction extending from the optical input to the optical output of the probe This fourth segment solely comprises:

a layer formed solely from the silicone jacket 13.

This fourth segment comprises the end of the probe forming the optical output. It will be noted that the end of the tube defines the end of the third segment.

This fourth segment S4 advantageously ends with an atraumatic end. The light output from the core of the optical fiber passes through this fourth segment. Depending on the targeted application, this fourth segment may comprise or play the role of an optical diffuser.

Second Embodiment—FIG. 1B

This second embodiment differs from the first embodiment in that the tube 14 has been replaced by complete over-molding in silicone. The process employed will thus be different. It will not be a question of filling the tube with silicone but of over-molding silicone around the optical fiber.

In this second embodiment, starting from the internal layer closest to the axis and moving toward the external layer, which is the layer furthest from the axis of the probe, the various segments are described below.

The probe comprises the same connecting segment (section Sc) advantageously forming the optical input of the device.

The connecting segment solely comprises:

a first layer formed from the core 10 of the optical fiber;

a second layer formed from the cladding 11 of the optical fiber;

a third layer formed from an epoxy adhesive 15;

a fourth layer formed from a ferrule 16 allowing the optical connection to the light source; the epoxy adhesive allows the ferrule to be adhesively bonded to the second layer (cladding of the optical fiber).

In this connecting segment, it is proposed to strip the optical fiber over at least one portion of its length in order to remove its protective coating and allow the ferrule to be adhesively bonded.

The probe comprises a first segment (section S10) extending the connecting segment.

This first segment solely comprises:

a first layer formed from the core 10 of the fiber;

a second layer formed from the cladding 11 of the optical fiber;

a third layer formed from the protective coating 12 of the optical fiber;

a fourth layer composed of the silicone jacket 13 over-molded around the fiber.

This first segment is intended to remain in the extra-cortical region of the living being and will be bent during its implantation to form a dog-leg therein. The first layer, the second layer and the third layer form the optical fiber such as described above. To improve the mechanical protection, the protective coating of the fiber is kept in this first segment.

The probe comprises a second segment (section S20) extending the first segment in the direction extending from the optical input to the optical output of the probe.

This second segment solely comprises:

a first layer formed from the core 10 of the fiber;

a second layer formed from the cladding 11 of the optical fiber;

a third layer formed from the silicone jacket 130.

The second segment is intended to penetrate into the intracerebral region. It is in this second segment that the optical fiber is stripped to remove its protective coating 12, thus allowing this segment to be made more supple and more seal-tight.

The probe comprises a third segment (section S30) extending the second segment in the direction extending from the optical input to the optical output of the probe.

This third segment solely comprises:

a first layer formed from the silicone jacket 130.

In this embodiment, this third segment S30 comprises the end of the probe forming the optical output.

This third segment S30 advantageously ends with an atraumatic end. The light output from the core of the optical fiber passes through this third segment. Depending on the targeted application, this third segment may comprise or play the role of an optical diffuser.

In order to guarantee that the fiber is correctly positioned at the center of the probe, spacers (rings, spirals, etc.) may be regularly positioned along the fiber. These spacers will preferably be made of the same material as the silicone over-molding 130.

According to one particular aspect of the invention, in both embodiments, it will be noted that the first segment (sections S1, S10) and the second segment (sections S2, S20) allow the probe 1 to have an architecture that is both supple and flexible enough in the implanted region to avoid any impact or trauma on the tissues in question and stiff enough outside the implanted region to avoid any breakage.

According to one particular aspect of the invention, the jacket 13, 130 and the protective coating 12 have different mechanical characteristics and their functions are also very different. The jacket layer notably allows the probe to be given seal-tightness characteristics that the protective coating of the optical fiber is unable to provide and the probe to be given its atraumatic end.

Nonlimitingly, the various components of the probe will have the following mechanical characteristics:
ETFE: Shore D hardness of 62 to 72, Young's modulus ranging from 300 to 800 MPa.
Silicone: Shore A hardness of 30 to 80 (preferably 50), Young's modulus ranging from 1 to 2 MPa.

Moreover, the removal of the protective coating 12 over a portion of the length of the probe, as proposed above, may have a plurality of advantages. A first advantage resides in the improvement in the flexibility of the probe in the stripped segment. A second advantage resides in the improvement in seal-tightness, allowing the introduction of any liquid to be avoided. Specifically, silicone notably proves to be a material that adheres better to the cladding layer of the optical fiber than the protective coating thereof (which is made of ETFE).

To facilitate the definition of the amount of light output from the probe, it is necessary to correctly position, lengthwise and with respect to centrality, the optical fiber in the probe. Advantageously, the second segment may thus comprise a member 17 for centering the core 10 of the fiber and its cladding 11, positioned around the stripped optical fiber. This centering member may be made of a radiopaque material (for example: platinum, stainless steel) in order to allow the position of the probe to be precisely controlled by radiography during surgery or to allow monitoring post-surgery.

In the first embodiment (section S2'), this centering member 17 is arranged, on the one hand, so as to bear against the cladding 11 of the optical fiber and, on the other hand, so as to be separated from the tube 14 by a jacket layer 13 made of silicone.

In the second embodiment (section S20'), the silicone 130 also jackets the centering member 17, in addition to the optical fiber.

This centering member will notably allow the role of shim to be played with respect to the optical fiber (10+11), whether in the tube 14 during the filling process or during the over-molding.

Figure 3A:
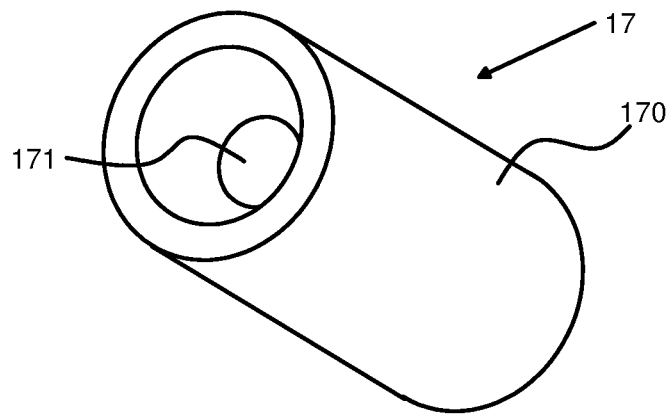
FIGS. 3A to 3C show various variant embodiments of a centering member employed in the probe of the device of the invention.
Figure 3B:
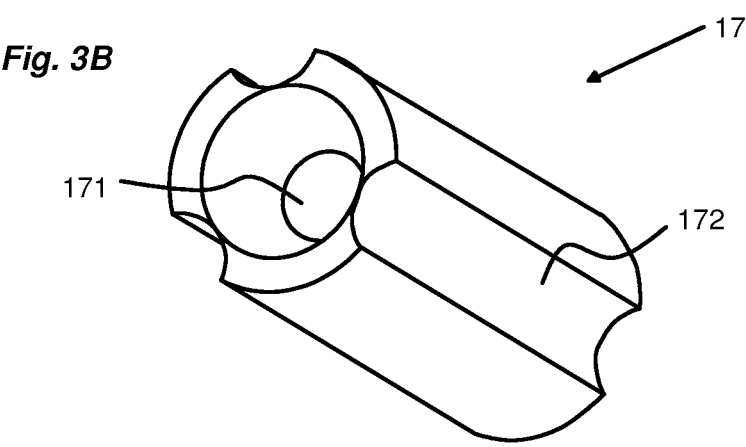

The centering member 17 may comprise a sleeve 170 having a longitudinal central channel 171 into which the core of the optical fiber and its cladding (FIGS. 3A and 3B) are inserted.

The sleeve may comprise one or more external, and for example longitudinal (FIG. 3B) or helicoidal, lateral grooves 172. Each groove 172 is arranged to allow the silicone to flow through the tube 14, during the filling in the case of the first embodiment and to serve as an anchor in the case of the second embodiment.

Figure 3C:
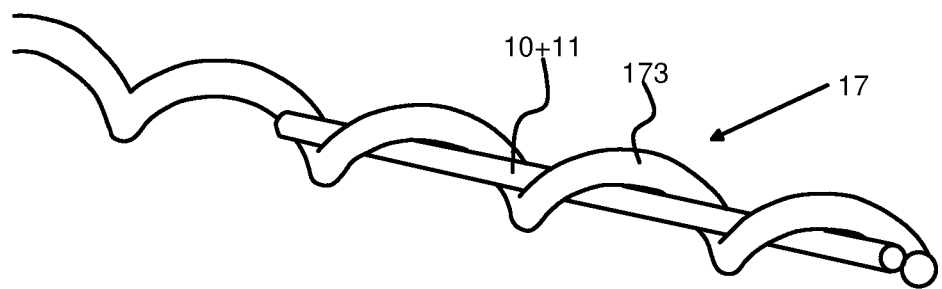

The centering member 17 may comprise a helix-shaped part 173 (designated the spiraled shim below) wound around the core 10 of the optical fiber and the cladding 11 thereof (FIG. 3C). This embodiment will be particularly advantageous when the probe is formed with over-molding and the spiraled shim is made of silicone. To facilitate the manufacture of the probe while guaranteeing the centeredness of the fiber and the feasibility of the over-molding, while avoiding rework of the final part, this shim may be produced beforehand and assembled with the optical fiber before being placed in the over-molding mold. The spiraled shim will also allow a relative suppleness to be preserved over the entire length of the probe.

Nonlimitingly, the spiraled shim, which is made of biocompatible material, may be made of stainless-steel wire, iridium-coated platinum, or by extrusion of silicone or acrylate.

This spiraled shim may have a square or rectangular section or a substantially square section, the two opposite sides of which are curved. One of these two sides thus has a radius of curvature tailored to the outside diameter of the optical fiber (core+cladding) and the other of these two sides may have a radius of curvature tailored to the inside diameter of the tube 14. This solution will notably allow the outlines of the tube and of the fiber to be more closely followed and will limit the risk of crack initiation.

The spiraled shim may be of a variable length. It may extend from the connecting segment to the end of the optical fiber, at the far end. At the far end, it may stop at the same point as the stimulating optical fiber, or upstream thereof in the optical sense.

The centering member 17 will advantageously be produced with a radiopaque marking, so as to check the probe is correctly positioned during its surgical installation.

The device may comprise at least one optical feedback system allowing a measurement of the optical power generated at the end of the probe to be transmitted. This optical feedback solution may be employed in the context of the first embodiment and of the second embodiment.

This system comprises at least one optical fiber 18 that is advantageously wound helically around the stimulating optical fiber (10, 11), in order to return an optical signal from the optical output to the optical input. This fiber will thus perform, in addition or alternatively, the role of centering member such as defined above and shown in FIG. 3C and its shape will not form an obstacle to the flow of the silicone 13 during the over-molding. On the side of the optical input, the feedback optical fiber is advantageously held in the ferrule and is assembled with the optical connector that is intended to be connected to the optical base.

Figure 4A:
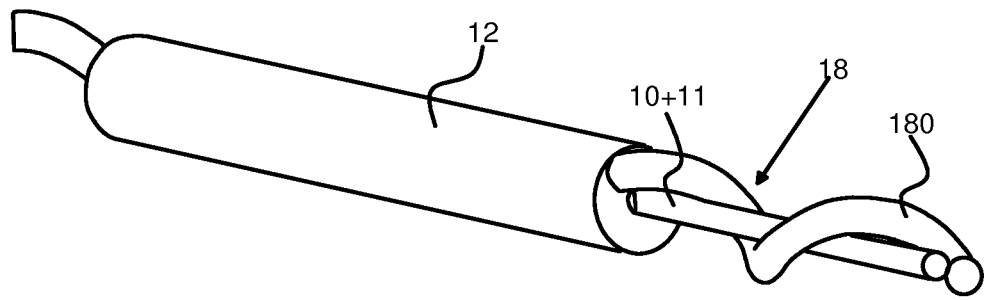
FIGS. 4A to 4D show various variant embodiments of an optical feedback system employed in the device of the invention.
Figure 4B:
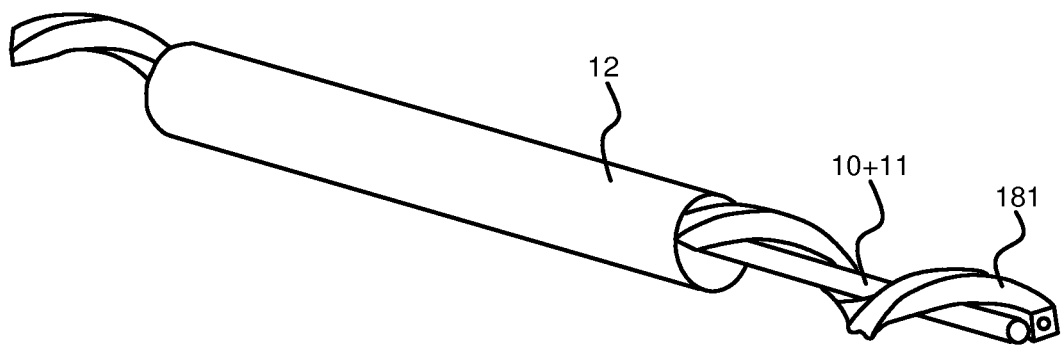
Figure 4C:
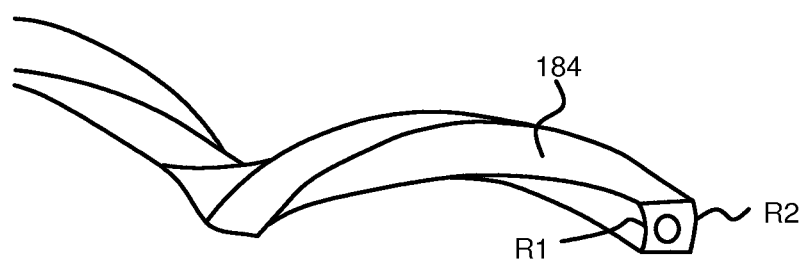

This feedback optical fiber 18 may have various configurations:
- a core of circular section and a cladding of circular section (180—FIG. 4A);
- a core of circular section and a cladding having a section of rectangle shape, and advantageously of square shape (181—FIG. 4B);
- a core of circular section and a cladding having a substantially square section, the two opposite sides of which are curved (184—FIG. 4C). One of these two sides may thus have a radius of curvature R1 tailored to the outside radius of curvature of the optical fiber (core+cladding) and the other of these two sides may have a radius of curvature R2 tailored to the inside radius of curvature of the tube 14. This solution will notably allow the outlines of the tube and of the fiber to be more closely followed and the risk of crack initiation to be limited.

Figure 4D:
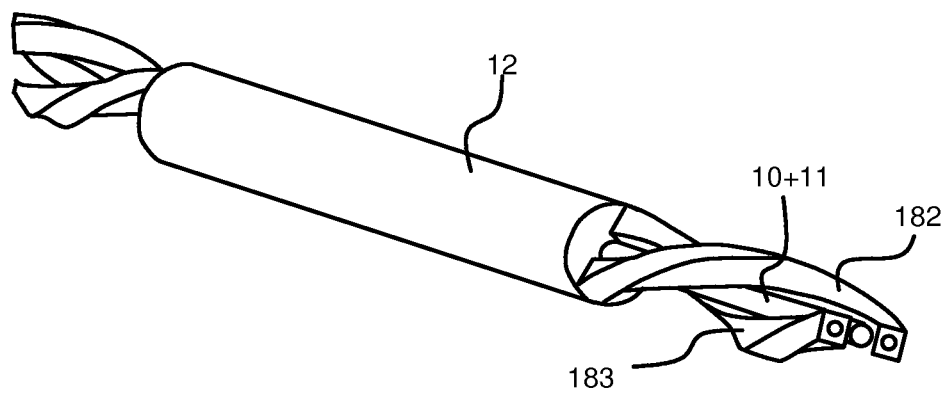

The system may also comprise two feedback optical fibers 182, 183 wound helically around the stimulating optical fiber (FIG. 4D). The two optical fibers will possibly have a section of identical shape and/or identical dimensions or not, for example with a core of circular section and a cladding such as defined above with reference to FIGS. 4A to 4C. Likewise, they will possibly complete an existing centering member or replace it in order to hold and center the optical fiber during the manufacture.

Each feedback optical fiber comprises an input optical end via which the optical signal is captured and an output optical end via which the captured optical signal is collected.

The two helices formed by the two optical fibers advantageously have an identical helix pitch and are interlaced around the stimulating optical fiber.

The two fibers 182, 183 will possibly end at a different distance from the distal end of the probe in order to evaluate the optical feedback at different distances from the point of emission. At the near end, the two feedback optical fibers are advantageously held in the ferrule and assembled with the optical connector that is intended to be connected to the optical base.

The stimulating optical fiber and the two feedback optical fibers are embedded at least over some or over the entirety of the length of the probe in the silicone jacket, and preferably over the entire length of the probe, both in the context of the first embodiment and in the context of the second embodiment.

According to one particular aspect of the invention, the spiraled shim solution (in the form of a feedback optical fiber or not) notably allows slip of the two elements against each other to be limited, notably when the probe is dog-legged.

With reference to FIG. 5, in the tube-based first embodiment 14, a plurality of solutions may be envisioned with respect to forming the last segment (section S4) of the device, at its far end:

A: a first solution consists in adhesively bonding a solid silicone part 19 of hemispherical (or oblong) shape to the end of the third segment (section S3); the fiber may be centered using a specific centering member 17 such as described above;

B: a second solution consists in depositing, via surface tension, a droplet 20 of silicone on the end of the third segment; the fiber may be centered using a specific centering member 17; this solution may be implemented during the filling of the tube or a posteriori;

C: a third solution consists in producing a solid part 21 made of silicone (epoxy or any other material that remains stable in tissues) by molding so as to form an optical-quality plug that is pushed into the tube of the second segment up to the end of the optical fiber; the fiber (core+cladding) may be centered using a specific centering member 17;

D: a fourth solution consists in producing a solid part 22 made of silicone (epoxy or any other material that remains stable in tissues—and which will be transparent or scattering depending on the application) by molding and in adding it by adhesive bonding in such a way as to push it into the tube until the end of the fiber is encircled; the part also comprises an internal channel into which the end of the fiber (core+cladding) may be pushed, and which then plays the role of centering member; the tube 14 will possibly be radiopaque;

E: a fifth solution consists in producing a silicone dome that is cohesive with the silicone filling of the tube; thus, the far portion of the probe will be made at the same time as the tube is filled. To make this achievable, it is recommendable to fill the tube (E-1) over its entire length with un-crosslinked silicone 130 (the tube already housing the stimulating optical fiber, the centering member and the optional feedback optical fibers), to set the silicone filling of the tube via localized drying (S-L) (with a hot-air gun for example) beyond the centering ring (E-2) on the side from which filling occurs, so as to prevent the silicone from flowing from the tube in the step of producing the dome, then to cut the end of the tube to the desired length (optional step), and to deposit a calibrated amount of silicone 25 in order to form the hemispherical portion (E-3). Subsequently, the entirety of the probe and of the dome is crosslinked (for example in an oven), thus making the dome cohesive with the interior of the probe (E-4). This solution has the advantage of guaranteeing a very good cohesion of the probe. The risk of detachment of the dome that exists in the case of a dome added adhesively, which would be a danger notably in the case of intracerebral implantation, is minimized.

In the first embodiment of the optical probe, according to one particularity, the distance (L) between the end of the tube 13 and the end of the core of the optical fiber on the far side allows the power density at the end of the device to be varied. Since the tube is made of silicone that is not optical grade, it will be necessary to take care to ensure that the third segment (section S3) is not too long in order to prevent the light ray output from the optical fiber (of the second segment—section S2) from striking the internal wall of the tube 14. This distance will for example be 2.5 mm (with a possible variation of +/−0.25 mm).

The device may comprise a stopping system intended to adjust the level of penetration of the probe during the implantation (FIGS. 6A and 6B). This solution allows the probe to be placed manually, without risk to the patient, and is applicable to both embodiments of the device.

This stopping system is intended to bear against the surface of the neuroguide positioned beforehand on and fastened to the skull during the implantation and thus allows the level of penetration of the device to be adjusted and stopped.

Depending on the embodiment, this system may be adhesively bonded to or integrated into the optical probe.

This system comprises a member, such as a sleeve 23, which is fastened to the tube 14 of the device or to the over-molded jacket 130, and one or more spacers 24a, 24b of different lengths placed between said member and the extra-cortical region with a view to adjusting the penetration length of the probe. FIG. 6A thus shows a first configuration with a spacer 24a of a first length and FIG. 6B shows a second configuration with a spacer 24b of a different length to that of the first configuration. By varying the length of the spacer, it is thus possible to adjust the position of the stop formed by the sleeve 23 against another stop.

The sleeve 23 will possibly be made of various materials: silicone, metal (titanium, stainless steel) or plastic (PEEK for polyether ether ketone), etc.

The invention thus has many advantages, among which:
- a probe perfectly suited to long-term implantation, which is not only seal-tight, but also solid and supple in the particularly sensitive region;
- the use of various types of materials of optical quality (silicone, PU, etc.) such as described above allows a device to be produced that is compatible with installation in the brain and particularly in the third ventricle through one of the lateral ventricles;
- a solution that is easy to manufacture, whether by injection into the tube or by over-molding;
- a reliable solution, notably obtained by virtue of perfect positioning of the various elements, by virtue of the centering member;
- a probe allowing an effective treatment, notably by virtue of the optical feedback solution, the latter moreover being particularly compact.

The invention claimed is:

1. An implantable illuminating device to be implanted in a living being to locally illuminate a region of said living being, said device comprising:

a probe that is elongate along a longitudinal axis between a near end and a far end, said probe being a rod of circular cross section of constant diameter overall a length of the probe, the probe including a stimulating optical fiber that comprises a core, a cladding, and a protective coating, and a jacket, wherein the probe further includes a plurality of successive segments along the longitudinal axis, each segment having a cross section containing a plurality of concentrically superposed layers, wherein the cross section of each segment includes a plurality of superposed layers that is different from the cross section of each adjacent segment, wherein the segments include
- a first segment along which said stimulating optical fiber is covered by the jacket, wherein the cross section of the first segment includes a first layer including the optical-fiber core, a second layer including the optical-fiber cladding, a third layer including the protective optical-fiber coating, a fourth layer including the jacket, and an external fifth layer composed of a tube,
- a second segment extending from said first segment, in which said stimulating optical fiber in the second segment does not include the protective coating but includes only the core and the optical cladding covered by the jacket, wherein the cross section of the second segment includes a first layer including the core of the optical fiber, a second layer formed from the cladding of the optical fiber, and a third layer including the jacket,
- a third segment extending from said second segment, wherein the cross section of the third segment includes only a first layer comprising said jacket and a second layer comprising the tube, and
- a terminal segment extending from the third segment and including only said jacket, said terminal segment including the far end of the probe, wherein the far end is configured so as to be atraumatic.

2. The device as claimed in claim 1, wherein the tube is made from a radiopaque material.

3. The device as claimed in claim 1, further comprising a connecting segment, located upstream of the first segment, the section of which comprises a first layer formed from the core of the fiber, a second layer formed from the optical-fiber cladding, a third layer Ruined from an adhesive and a fourth layer formed from a ferrule.

4. The device as claimed in claim 1, further comprising a light source to which is optically connected to the probe via the near end.

5. The device as claimed in claim 1, further comprising a stopping member associated with at least one spacer in order to adjust a penetration of the probe and a position of the far end.

6. The device as claimed in claim 1, further comprising at least one centering member to center the stimulating optical fiber, said centering member being positioned around said optical fiber and arranged to form a shim for said optical fiber.

7. The device as claimed in claim 6, wherein said centering member comprises a cylindrical sleeve having a central channel in which is inserted said optical fiber.

8. The device as claimed in claim 6, wherein said centering member comprises a cylindrical sleeve having one or more external lateral grooves.

9. The device as claimed in claim 6, wherein said centering member comprises a part of helical shape that is wound around the core of the optical fiber and its cladding.

10. The device as claimed in claim 6, wherein said centering member is made of a radiopaque material.

11. The device as claimed in claim 1, further comprising an optical feedback system comprising at least a first feedback optical fiber comprising an input optical end configured to capture an optical signal and an output optical end configured to transmit the captured optical signal, said first feedback optical fiber being wound helically around the stimulating optical fiber over at least one portion of the length of said stimulating optical fiber.

12. The device as claimed in claim 11, wherein the optical feedback system comprises a second feedback optical fiber wound helically around said stimulating optical fiber and comprising an input optical end and an output optical end.

13. The device as claimed in claim 6, wherein the input optical end of the first feedback optical fiber and the input optical end of the second feedback optical fiber are located at different lengths from the optical output of the stimulating optical fiber.

14. The device as claimed in claim 6, wherein each feedback optical fiber comprises a core of circular section and an optical cladding having two curved opposite sides, one of the two sides having a first radius of curvature and the other of the two opposite sides having a second radius of curvature different from the first radius of curvature.

15. A process for fabricating an implantable illuminating device such as defined in claim 1, the process comprising the following steps:

- filling the tube with an un-crosslinked jacket material,
- at least partially drying the un-cross linked jacket material in order to set it inside the tube,
- depositing a calibrated amount of un-crosslinked jacket material in order to form said terminal segment,
- crosslinking the jacket material over the entire length of the probe.

* * * * *